United States Patent [19]
Scott et al.

[11] Patent Number: 5,316,246
[45] Date of Patent: May 31, 1994

[54] INTRAVENOUS TUBE HOLDER

[75] Inventors: James Scott; Chet Ross, both of Tucson, Ariz.

[73] Assignee: Scott/Ross Designs Inc., Tucson, Ariz.

[21] Appl. No.: 855,777

[22] Filed: Mar. 23, 1992

[51] Int. Cl.[5] .............................................. A61M 39/00
[52] U.S. Cl. ................................... 248/68.1; 248/74.2; 248/75; 248/90
[58] Field of Search ................... 248/75, 87, 90, 74.2, 248/68.1; D24/128

[56]             References Cited
U.S. PATENT DOCUMENTS

| | | | |
|---|---|---|---|
| D. 243,477 | 2/1977 | Cutruzzula et al. | D24/128 |
| D. 260,850 | 9/1981 | Greenblatt | D8/356 |
| D. 263,624 | 3/1982 | Stenzler et al. | D24/128 |
| D. 265,508 | 7/1982 | Rusteberg | D24/128 |
| D. 269,121 | 5/1983 | Pollard | D24/128 |
| D. 290,041 | 5/1987 | Scott | D24/128 |
| 3,906,592 | 9/1975 | Sakasegawa et al. | 248/68.1 |
| 4,114,241 | 9/1978 | Bisping | 248/68.1 X |
| 4,160,473 | 7/1979 | Winchell | 150/0.5 |
| 4,167,211 | 9/1979 | Haller | 248/68.1 X |
| 4,308,642 | 1/1982 | Heyman | 248/68.1 X |
| 4,381,764 | 3/1983 | Wojcik | 248/68.1 X |
| 4,397,641 | 8/1983 | Jacobs | 604/180 |
| 4,453,933 | 6/1984 | Speaker | 604/179 |
| 4,579,310 | 4/1986 | Well et al. | 248/68.1 X |

FOREIGN PATENT DOCUMENTS 12916 10/1903 Norway .................. 248/90

Primary Examiner—Richard K. Seidel
Assistant Examiner—Kenneth E. Peterson
Attorney, Agent, or Firm—Ogram & Teplitz

[57]             ABSTRACT

An intravenous tube holder having positioned along one edge, a plurality of clips for securing the holder to an intravenous tube. On the opposite edge, a writing surface is provided for either the writing of medical instructions or for the attachment of a label giving identification and instructions as to the medicine being delivered via the intravenous tube. At one end of the holder is a male receptacle, at the other end is a female receptacle; this combination permits the holders to be interconnected into a gang approach so as to keep the various intravenous tubes from several bottles orderly and easily identified. In one embodiment of the invention, the holder is color-coded to provide quick identification of the medicine or its characteristics.

17 Claims, 2 Drawing Sheets

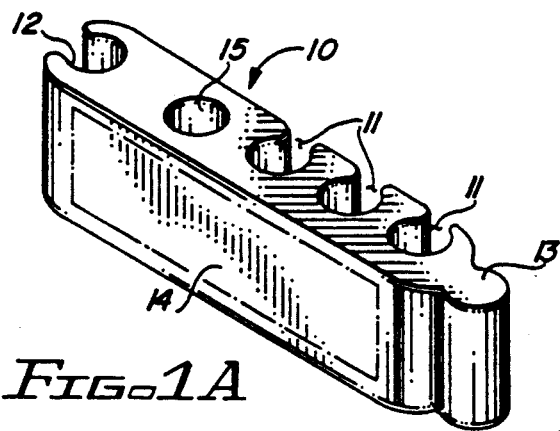
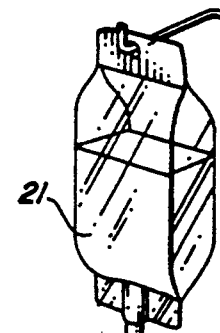
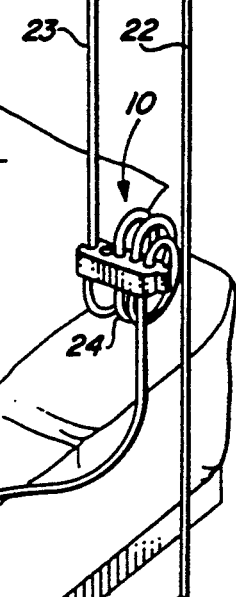
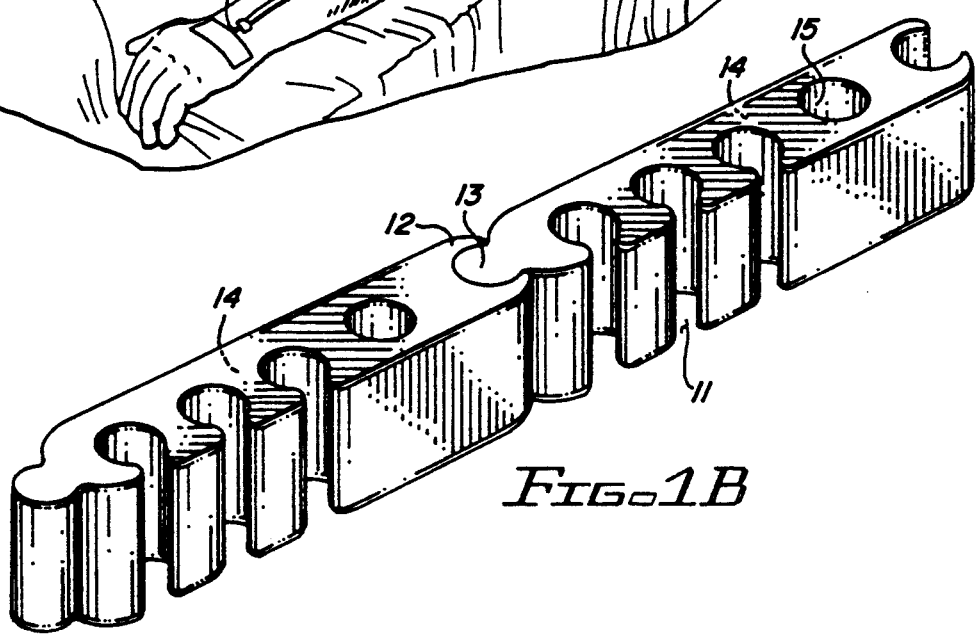
FIG. 1A
FIG. 2
FIG. 1B

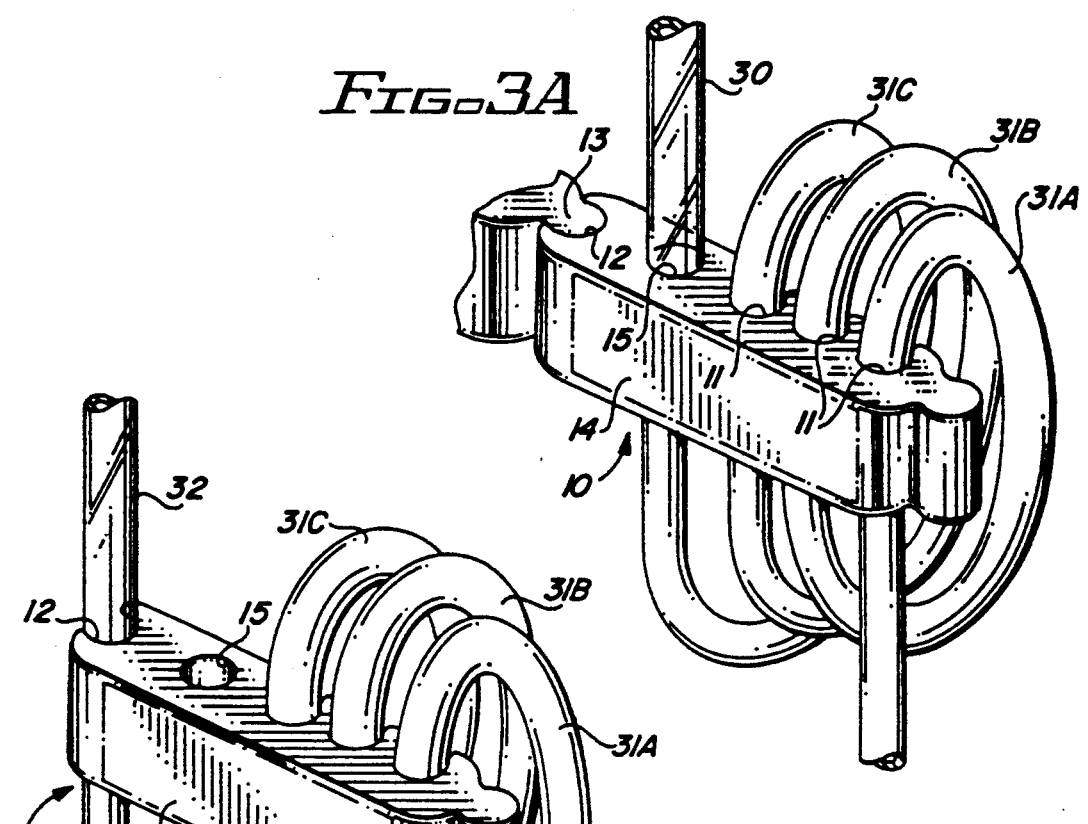
FIG-3A
FIG-3B
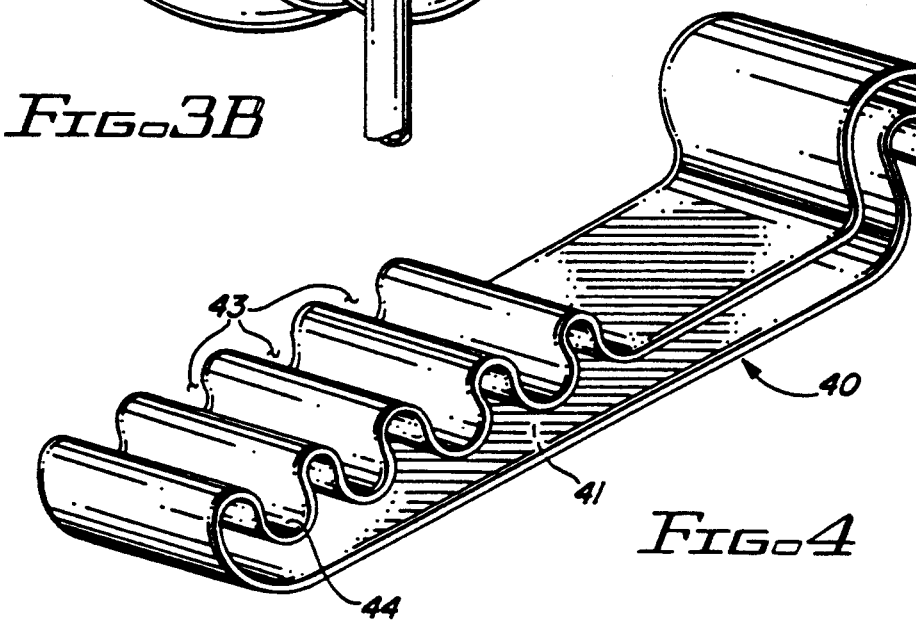
FIG-4

INTRAVENOUS TUBE HOLDER

BACKGROUND OF THE INVENTION

This invention relates generally to the medical field and more particularly to intravenous (IV) tubes and their use.

The delivery of medicines and fluids to a patient is one of the most critical aspects of intensive medical treatment. This delivery is typically via the use of a intravenous feed line which communicates the therapeutic liquid (whether the liquid is saline water or medicine) from a bottle/bag to a hollow needle via a flexible tubing. The hollow needle is inserted into the patient's vein for the slow application of the therapeutic liquid.

Although the procedure is well established and normally operates without flaw, there are situations which make the monitoring of these fluids and their delivery very difficult.

At least three times a day the nursing staff is relieved by the next shift. Since it is the nursing staff which monitors the IV delivery, each new shift must become familiar with the multitude of patients and the variety of IV drugs being administered.

A floor nurse can have responsibility for up to forty different patients, each of them having anywhere from one to eight different IV drugs being administered. Currently, adhesive tape is added to the IV tube permitting the nurse to write information about the drug and its delivery. This means though that the nurse must adjust the often curled tape so that it can be read.

Additionally, if there is a variety of IV drugs being administered, their respective tubing often becomes entangled and confused. This entanglement may become life threatening if it takes the nurse time to identify which tube connects to which IV bottle.

In an attempt to clear away the confusion, a variety of inventions have been developed which try to keep the tubing orderly. One such approach is described by U.S. Pat. No. 4,160,473, entitled "Plastic Container with Auxiliary Tube Retention Means" issued to Winchell on Jul. 10, 1979. This device wraps the IV tube around the bag/bottle to take up the slack.

Unfortunately, this arrangement does not assist in marking of the IV tube. Further, this arrangement can injure the patient when the patient rolls or moves; the IV tube cannot "give" or expand so the needle is pulled out of the patient.

Other approaches have attempted to secure the IV tube through the use a clamp or support type of mechanism. Examples of these approaches include: U.S. Pat. No. Des. 260,850, entitled Medical Flexible Tube Support" issued to Greenblatt on Sep. 22, 1981; U.S. Pat. No. Des. 243,477, entitled "Intravenous Tube Anchor" issued to Cutruzzula et al. on Feb. 22, 1977; and, U.S. Pat. No. Des 263,624, entitled "Adjustable Medical Tubing Support Frame or Similar Article" issued to Stenzler et al. on Mar. 30, 1982.

In all of these approaches, the tube is secured but the flexablity permitting the patient to roll or move is not present. Furthermore, marking of the tubing is even more difficult since these devices are bulky and complex.

To allow the patient to move, a variety of techniques have secured the IV tube to the patient through the use of a bracelet approach. This approach is exemplified by: U.S. Pat. No. 4,453,933, entitled "Intravenous Device" issued to Speaker on Jun. 12, 1984; U.S. Pat. No. Des 290,041, entitled "Intravenous Tube Holder" issued to Scott on May 26, 1987; and, U.S. Pat. No. 4,397,641, entitled "Catheter Support Device" issued to Jacobs on Aug. 9, 1983.

Although those devices do prevent the hollow IV needle from being pulled from the patient, in use, as the patient rolls, the pull on the tubing causes the IV bottle and support bracket to be pulled over. This is an even more dangerous situation than if the needle had been pulled out.

To address this issue, a variety of devices have been designed to more securely affix the IV bottle. These include: U.S. Pat. No. Des 265,508, entitled "Combined Bottle Neck Clamp and Tube Holder" issued to Rusteberg on Jul. 20, 1982; and U.S. Pat. No. Des 269,121, entitled "Retractable IV Container Holder" issued to Pollard on May 24, 1983.

The basic structure of these patents result in the IV tubing being even less flexible since the tubing is more securely fastened to the IV bottle and support. This only restricts the patients movement more.

It is clear that there does not exist an IV holder which permits movement of the patient without the threat of injury and also allows for easy marking/labeling and organization of single or multiple IV tubes simultaneously.

SUMMARY OF THE INVENTION

The present invention creates an intravenous tube holder having positioned along one edge a plurality of clips for securing the holder to an intravenous tube. These clips are open at one side. This opening permits the IV tube to be securely fastened, but, should the patient move, the "tug" on the IV tube readily releases the IV tube from the holder.

In this manner, the tugging action is expended at the holder, not the hollow IV tube or the IV rack and bottle.

On the opposite edge, a writing surface is provided for either the writing of medical instructions or the attachment of a label giving identification and instructions as to the medicine being delivered via the intravenous tube. This writing surface is a flat area (possible textured to accept ink from a pen) and due to its position on the opposite side of the clips, the surface is readily visible to the nurse.

In one embodiment of the invention, the holder is color coded to provide quick identification of the medicine or its characteristics. This is particularly useful to designate "benign" liquids (e.g. saline solution) from critical medicines which need more monitoring (e.g. anti-cancer drugs).

At one end of the holder is a male receptacle, at the other end is a female receptacle; this combination permits the holders to be interconnected into a gang approach so as to keep the various intravenous tubes from several bottles orderly and easily identified. This attribute is particularly useful when there is more than one IV medicine being administered to the patient.

Each IV tube has its own IV tube holder, but, the various holders are easily and conveniently grouped for ease in reading and in identification.

The holders are constructed from a variety of materials obvious to those of ordinary skill in the art. These materials include plastic, metal, paper products, and cardboard. The weight of the holder is a consideration in the choice of materials but due to the overall size of the holder, weight usually does not become a problem.

One embodiment of the invention is constructed of a readily biodegradable material permitting the invention, once it is disposed in a land-fill of the like, to readily breakdown. This aspect reduces problems for the hospital when faced with disposal of the spent or broken holders.

The invention, together with various embodiments thereof, will be more fully explained by the following drawings and their descriptions.

DRAWINGS IN BRIEF

FIG. 1A is a perspective view of the preferred embodiment of the invention.

FIG. 1B illustrates the preferred embodiment arranged in a gang approach.

FIG. 2 is a perspective view of an embodiment of the invention in use with a patient.

FIGS. 3A and 3B illustrate the clip operation of the invention relative to an IV tube.

FIG. 4 is a perspective view of an alternative embodiment of the invention.

DRAWINGS IN DETAIL

FIG. 1A is a perspective view of the preferred embodiment of the invention.

Holder 10 has a plurality of clips 11 on a first surface. Clips 11 are used to secure the IV tubing. Clips 11 are structured to provide sufficient frictional clasping of the IV tubing to prevent the tubing from falling away, but not so much friction that upon movement by the patient, the tubing is not readily released from clips 11.

On an opposite side of clips 11, is marking surface 14. Marking surface 14 is suitable for either writing directly thereon or for the placement of a tape or label to mark the medicine being administered.

Male extension 13 is designed to interlock with a female receptacle 12. Hole 15 is used in some embodiments for accepting the IV tube therethrough. Use of hole 15 is beneficial when the holder is packaged with the IV solution and tubing at the laboratory or factory.

FIG. 1B illustrates the preferred embodiment arranged in a gang approach.

As noted, the same embodiment as described relative to FIG. 1A is interlocked, via male extension 13 and female receptacle 12. In this manner, any number of holders are combined.

In some situations, the additional holder is used to secure a second or third (or more) IV tube; but, at times there is a need for further marking of the IV tube, in this case a second holder is used to provide more writing space or to add further warnings.

The holder is also particularly useful if two IV tubes drain into a common feeder tube. Labeling of the tubes (and hence their solutions) becomes critical should it become necessary to trace a drug which is causing a negative reaction.

In the case where the holder is color coded, a red holder would signifies that the drug being administered is critical and should be monitored closely. Even some otherwise benign liquids (in this example marked with a "blue" holder) might be dangerous to susceptible patients. As example, a glucose liquid being administered to a diabeticly prone patient must be very closely monitored; although glucose is normally benign, in this case a "red" warning holder would be added to note the danger.

FIG. 2 is a perspective view of an embodiment of the invention in use with a patient.

Patient 20 is being administered medicine via IV bottle 21 and IV needle 25. Tubing 23 connects the IV Bottle 21 with the needle 25. IV stand 22 holds the IV bottle 21.

As shown here, excess tubing 24 is would up and held by holder 10, as already described.

FIGS. 3A and 3B illustrate the clip operation of the invention relative to an IV tube.

FIG. 3A illustrates an embodiment of the invention wherein holder 10 has IV tube 30 inserted through hole 30. This structure is used when the holder 10 is manufactured and packaged with the IV tubing.

The structure of FIG. 3A also permits a male extension 12 from another holder to engage female receptacle 13 so that several holders may be locked together.

Excess IV tubing is secured to clips by way of a looping arrangement as illustrated by loops 31A, 31B, and 31C.

FIG. 3B illustrates the situation where holder 10 and IV tube 32 are delivered to the hospital as separate products. In this embodiment, female receptacle 12 is used as the initial clip to IV tube 32. Hole 15 is left empty.

FIG. 4 is a perspective view of an alternative embodiment of the invention.

In this embodiment, clips 42 are in the same plane as the female receptacle 44. Male extension 43 is designed to engage female receptacle 44.

Writing surface 41 lies on the opposite side.

It is clear that the present invention provides for an improved and safe method for organizing and labeling IV tubes.

What is claimed is:

1. An intravenous tube holder for securing an intravenous tube, said intravenous tube holder comprising a body member having positioned along one edge thereof of a plurality of clip means for securing said body member to the intravenous tube, a male attachment means located on a first end of said body member, and a female receptacle means for receiving a male attachment means from a different tube holder, said female receptacle means located on a second end of said body member and is a clip means for securing said body member to the intravenous tube.

2. The intravenous tube holder according to claim 1 further comprising a labeling surface on a side opposite said plurality of clip means.

3. The intravenous tube holder according to claim 2 wherein said labeling surface is textured to accept ink.

4. The intravenous tube holder according to claim 3 further including an orifice in said body member for totally encircling said intravenous tube.

5. The intravenous tube holder according to claim 4 wherein said body member is color-coded.

6. An intravenous tube holder for securing an intravenous tube, said intravenous tube holder comprising a body member having,
   a) positioned along one edge, a plurality of clip means for securing said body member to the intravenous tube,
   b) a labeling surface on a side opposite said plurality of clip means,
   c) a male attachment means located on a first end of said body member, and
   d) a female receptacle means for receiving a male attachment means from a different body member, said female receptacle means located on a second end of said body member and is a clip means for securing said body member to an intravenous tube.

7. The intravenous tube holder according to claim 6 wherein said labeling surface is textured to accept ink.

8. The intravenous tube holder according to claim 7 further including an orifice in said body member for totally encircling said intravenous tube.

9. The intravenous tube holder according to claim 8 wherein said body member is color-coded.

10. A gang of intravenous tube holders for securing an intravenous tube from a plurality of intravenous bottles, each of said intravenous tube holders comprising a body member having,
 a) positioned along one edge, a plurality of clip means for securing said body member to the intravenous tube,
 b) a labeling surface on a side opposite said plurality of clip means,
 c) a male attachment means located on a first end of said body member, and
 d) a female receptacle means for receiving said male attachment means, said female receptacle means located on a second end of said body member and wherein selected ones of said male attachment means are interlocked with a female receptacle of a different intravenous tube holder and wherein said female receptacle is also a clip means for securing said body member to the intravenous tube.

11. The gang of intravenous tube holders according to claim 10 wherein said labeling surface is textured to accept ink.

12. The gang of intravenous tube holders according to claim 11 further including an orifice in said body member for totally encircling said intravenous tube.

13. The gang of intravenous tube holders according to claim 12 wherein said body member is color-coded.

14. An intravenous delivery system comprising:
 a) at least one intravenous bottle having a therapeutic fluid therein;
 b) a hollow needle inserted into a patient;
 c) an intravenous tube communicating said therapeutic fluid to said hollow needle and the patient; and,
 d) at least one intravenous tube holder, each of said intravenous tube holders having,
  1) positioned along one edge, a plurality of clip means for securing said body member to the intravenous tube,
  2) a labeling surface on a side opposite said plurality of clip means,
  3) a male attachment means located on a first end of said body member, and
  4) a female receptacle means for receiving a male attachment means from a different intravenous tube holder, said female receptacle means located on a second end of said body member, and wherein said female receptacle is also a clip means for securing said body member to the intravenous tube.

15. The intravenous delivery system according to claim 14 wherein said labeling surface is textured to accept ink.

16. The intravenous delivery system according to claim 15 further including an orifice in said body member for totally encircling said intravenous tube.

17. The intravenous delivery system according to claim 16 wherein said body member is color-coded based upon said therapeutic fluid.

* * * * *